(12) United States Patent
Van Geen

(10) Patent No.: US 7,336,362 B2
(45) Date of Patent: Feb. 26, 2008

(54) ARSENIC METER

(75) Inventor: Alexander Van Geen, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 49 days.

(21) Appl. No.: 10/523,568

(22) PCT Filed: Aug. 21, 2003

(86) PCT No.: PCT/US03/26484

§ 371 (c)(1),
(2), (4) Date: Jul. 29, 2005

(87) PCT Pub. No.: WO2004/019004

PCT Pub. Date: Mar. 4, 2004

(65) Prior Publication Data

US 2006/0007445 A1    Jan. 12, 2006

Related U.S. Application Data

(60) Provisional application No. 60/404,964, filed on Aug. 21, 2002.

(51) Int. Cl.
*G01N 21/25* (2006.01)
*G01N 21/00* (2006.01)

(52) U.S. Cl. ............ 356/407; 356/409; 356/432

(58) Field of Classification Search .......... 356/407, 356/409, 432, 434; 436/73, 74, 75, 177, 436/175; 210/752, 759, 902; 423/87
See application file for complete search history.

(56) References Cited

U.S. PATENT DOCUMENTS 4,797,000 A    1/1989    Curtis (Continued)

OTHER PUBLICATIONS

Johnson, D. L., and M. E. Q. Pilson,"Spectrophotometric Determination of Arsenite, Arsenate, and Phosphate in Natural Waters," Analytica Chimica Acta, 58, p. 289-299, 197.*

(Continued)

*Primary Examiner*—Roy M. Punnoose
(74) *Attorney, Agent, or Firm*—Baker Botts LLP; Manu J. Tejwani

(57) ABSTRACT

A field test-kit for analyzing arsenic concentration in water samples is provided. The kit includes a portable infrared beam photometer for measuring light absorbance in aqueous specimens. An infrared light emitting diode is configured to direct a beam of light through a specimen. A photodetector diode measures the intensity of light passing through the specimen. The photodetector output voltages relate to the light absorbed in the specimen and are displayed on a liquid crystal display screen. The kit is assembled using off-the-shelf electronic and opto-electronic components that have low power requirements. Dry cell batteries or solar cells power the kit. To test for arsenic, molybdenum based chemistries are used to selectively bind and convert arsenates and phosphates in the specimen into molybdenum-blue color complexes. The light absorbance of a specimen with both arsenates and phosphates bound in molybdenum-blue color complexes is compared to that of a reference specimen in which phosphates but not arsenates are bound and converted. The differential light absorbance of the two specimens is used to arrive at a quantitative value for the arsenic concentration in the water sample.

10 Claims, 9 Drawing Sheets

U.S. PATENT DOCUMENTS

| | | | |
|---|---|---|---|
| 4,847,066 A | * | 7/1989 | Honigs et al. ............. 424/10.3 |
| 5,059,790 A | | 10/1991 | Klainer et al. |
| 6,696,300 B1 | * | 2/2004 | Jaunakais et al. ............. 436/73 |

OTHER PUBLICATIONS

Johnson, D. L., and M. E. Q. Pilson,"Spectrophotometric determination of arsenite, arsenate, and phosphate in natural waters," Analytica Chimica Acta, 58, p. 289-299, 1972.

Chakraborty A. K. and Saha K. C. ,"Arsenical dermatosis from tubewell water in West Bengal," Indian J. Med. Res., 85, p. 326-334, 1987.

Guha Mazumder D. N. , Haque R. , Ghosh N. et al."Arsenic levels in drinking water and the prevalence of skin lesions in West Bengal," India. Int. J. Epidemiology, 27 (5), p. 871-77, 1998.

van Geen, A. et al., "Promotion of well-switching to mitigate the current arsenic crisis in Bangladesh," Bulletin of the World Health Organization, 2002, 80 (9).

Smith A. H. , Goycolea M. , Haque R. et al., "Marked increase in bladder and lung cancer mortality in a region of northern Chile due to arsenic in drinking water," Am. J. of Epidemiology, 147, p. 660-669, 1998.

Johnson, D. L., "Simultaneous determination of arsenate and phosphate in natural waters," Environmental Science and Technology, 5, pp. 411-414, 1971.

* cited by examiner

ARSENIC METER

CROSS-REFERENCE TO RELATED APPLICATION

This application is a national phase of International Patent Application No. PCT/US03/026484, filed Aug. 23, 2003, published on Mar. 4, 2004 as International Patent Publication No. WO 04/019004, which claims priority from U.S. patent application No. 60/404,964, filed on Aug. 21, 2002, each of which are incorporated by reference in their entireties herein, and from which priority is claimed.

BACKGROUND OF THE INVENTION

The present invention relates to devices and techniques for measuring arsenic concentrations, and more specifically for quantitative measurements of arsenic concentrations in aqueous solutions. The invention may be used to measure arsenic concentrations in groundwater.

A devastating health crisis is currently unfolding in Bangladesh and West Bengal, India, due to arsenic enrichment of groundwater supplied by millions of tubewells and used for human consumption. See e.g., British Geological Survey/Mott MacDonald Ltd. (U.K.), "Groundwater studies for arsenic contamination in Bangladesh," Final Report-Main Report, (1999). The arsenic enrichment is most, likely of natural origin. An estimated 25 million people are at risk of developing arsenic related health conditions that include skin lesions, respiratory illnesses and eye problems as early or intermediate disorders, as well as more deadly and debilitating long term diseases such as cancer of the skin, bladder, lung, and other internal organs, heart disease and neurological disorders. (See e.g., Chakraborty A. K. and Saha K. C., "Arsenical dermatosis from tubewell water in West Bengal," Indian J. Med. Res., 85, 326-334 (1987); and Guha Mazumder D. N., Haque R., Ghosh N. et al. "Arsenic levels in drinking water and the prevalence of skin lesions in West Bengal," India Int. J. Epidemiology, 27(5), 871-77 (1998). A number of governmental and non-governmental organizations are concerned about this mass arsenic poisoning related health crisis of unprecedented magnitude, and are seeking ways to address it (See e.g., van Geen, A., H. Ahsan, A. Horneman, R. K. Dhar, Y. Zheng, M. Stute, H. J. Simpson, S. Wallace, C. Small, M. F. Parvez, V. Slavkovich, N. J. Lolacono, A Gelman, M. Becker, A. Z. M. I. Hussain, H. Momotaj, M. Shahnewaz, K. M. Ahmed, and J. Graziano, "Well-switching: a remediation option worth promoting to reduce arsenic exposure in Bangladesh," Bulletin of the World Health Organization, submitted May 2001.

The problem of arsenic contamination of the groundwaters, which is now well publicized in the case of Bangladesh or West Bengal, is not limited to those geographical regions. Arsenic contamination of groundwaters is also found, and is of concern in other regions of the world. See e.g., Smith A. H., Goycolea M., Haque R. et al. "Marked increase in bladder and lung cancer mortality in a region of northern Chile due to arsenic in drinking water," Am. J. of Epidemiology, 147, 660-669 (1998).

A potential solution to alleviate the notable case of mass slow poisoning in Bangladesh and West Bengal, involves switching water consumption to safer wells that have no arsenic contamination or have arsenic contamination which is within acceptable "safe levels." Other solutions may involve treating contaminated groundwater to remove arsenic to make the water fit for human consumption. Arsenic levels of less than 50 µg/L are considered safe under official Bangladesh drinking water standards. More recent guidelines from the World Health Organization (WHO) recommend that arsenic levels be below 10 µg/L arsenic. In any case, there is an urgent need to accurately measure the arsenic concentrations in well waters to identify those that are unsafe due to arsenic contamination, as well as to identify those that are safe for use. Any solution will require on-going monitoring of water quality in the field.

Unfortunately, the safe arsenic levels of at most a few tens of µg/L are below the detection limits of conventional arsenic measurement devices and techniques that may be available or amenable for field use. For example, the "Merck field kit" (sold, for example, by EM Sciences, Merck KGaA, Darmstadt, Germany) has been widely used to measure arsenic. The Merck kit has an effective detection limit of about 100 µg/L. The Merck kits, and all other field kits commonly used, for example, in Bangladesh, are based on a mercuric bromide stain method. The method involves reducing or converting inorganic arsenic in solution into arsine gas. The arsine gas is collected and reacted with mercuric bromide on an indicator test strip. The color of the test strip changes from white, to yellow, or brown, according to the concentration of arsine it is exposed to. Estimates of the arsine concentration are obtained by visually identifying the color of the test strips. However, the color sensitivity to arsine concentration is poor, resulting in high detection limits. Efforts have been made to modify the arsine collection and exposure methods, to reduce the detection limits and to increase the sensitivity of the method. Also, indicator test strip chemistries have been improved to broaden the range of color responses. Modified field kits that are now available may include standard color charts for visual comparison. However, none of the modified or improved field kits have been satisfactory in the field. The modified methods often are complex and difficult to implement. The methods still call for visual identification of indicator test strip colors. The color sensitivity of the indicator test strips varies with the level of arsenic being measured. Different test strips may have to be used for different arsenic ranges, making continual adjustment or recalibration necessary according to the level of arsenic in the specimen. Results for samples containing arsenic levels in the range of 10 µg/L to 100 µg/L, are generally considered suspect. Further, the kits still utilize the chemistry that produces highly toxic arsine gas.

Consideration is now being given to other methods of accurately detecting arsenic levels in water samples. Attention is directed toward producing a sensitive field kit for quantitative detection of arsenic that retains it sensitivity over the wide range of arsenic concentrations found in groundwater. Attention is particularly directed toward adapting known laboratory chemical analysis or assay methods that do not produce toxic arsine gas as a byproduct in the testing groundwater for arsenic.

SUMMARY OF THE INVENTION

The present invention provides devices and methods for the detection of arsenic contamination in groundwater. The devices may be incorporated in to kits that are suitable for use in the field, for example, as hand-held colorimeters.

An exemplary colorimeter measures arsenic concentration by measuring the infrared absorption of color complexes formed by reacting the arsenic present in a water sample with suitable chemical reagents. The infrared absorption is measured using optical probes or channels. The colorimeter may have a two channel configuration (probes or channels A and B) to allow absorbance measurements on two test aliquots of a sample to be conducted in the same physical environment. The aliquots are placed in a pair of optical cuvettes. Solid state opto-electronic devices, for example, infrared light emitting diodes (LEDs), may be used to generate infrared radiation beams that are incident on the cuvettes. A pair of photodetectors placed on the side of the cuvettes across from the LEDs may be used to measure the intensity of radiation transmitted through the cuvettes. Conventional A/D converters may be used to process photodetector voltages into digital data for display or further processing. The photodetector output voltages may be displayed, for example, on a liquid crystal display (LCD), or on any other suitable output device. The colorimeter may include one or more microprocessors, to control the operation of various electronic components or to process measured data. A programmable interrupt controller (PIC) may, for example, be used to read photodetector voltages from the two channels sequentially. All of the electronic and optoelectronic components used in the colorimeter may be low power off-the-shelf components that are available commercially.

The method of quantitatively determining arsenic levels exploits the reactive properties of arsenic, which cause it to form part of a color complex according to its oxidation state (i.e., arsenate or arsenite). The color complexes utilized are "molybdenum-blue" complexes that do not incorporate arsenite, but incorporate both arsenates and similarly reactive phosphates that are present in solution in the water sample. The water sample may be treated with suitable reagents to either oxidize arsenic to the arsenate state or to reduce arsenic to the arsenite state. An unreduced or oxidized sample aliquot containing arsenates may be placed in one cuvette, while a reduced sample aliquot may be placed in the other cuvette as a reference. The differential absorbance of the two sample aliquots cancels the contribution of soluble phosphates to the absorbance and gives a quantitative measure of the arsenic concentration in the sample.

The molybdenum-blue color complexes that are utilized in the present method may be formed by adding suitable acidic chemical reagents (e.g. an acidified molybdate reagent and potassium antimonyl tartrate) to the water sample aliquots. The conventional chemical reagent chemistries that were previously designed and formulated for testing phosphate levels in seawater are especially modified or reformulated for application here to the measurement of arsenic in groundwater.

BRIEF DESCRIPTION OF THE DRAWINGS

Further features of the invention, its nature, and various advantages will be more apparent from the following detailed description of the preferred embodiments and the accompanying drawings, wherein like reference characters represent like elements throughout, and in which:

FIGS. 2a and 2b, are graphs of absorbance measured in a device channel and the differential absorbance as a function of the absorbance measured in the second device channel. The graphs illustrate the intrinsic performance of the device of FIG. 1a;

FIGS. 3a and 3b, are graphs illustrating the effect of humidity on channel readings of the device of FIG. 1a;

FIGS. 4a and 4b, are graphs illustrating the kinetics of color development and reagent stability in the device of FIG. 1a;

FIGS. 5a and 5b, are graphs illustrating the difference in color development for oxidized and reduced samples in the device of FIG. 1a;

DETAILED DESCRIPTION OF THE PREFERRED EMBODIMENTS

Figure 1A:
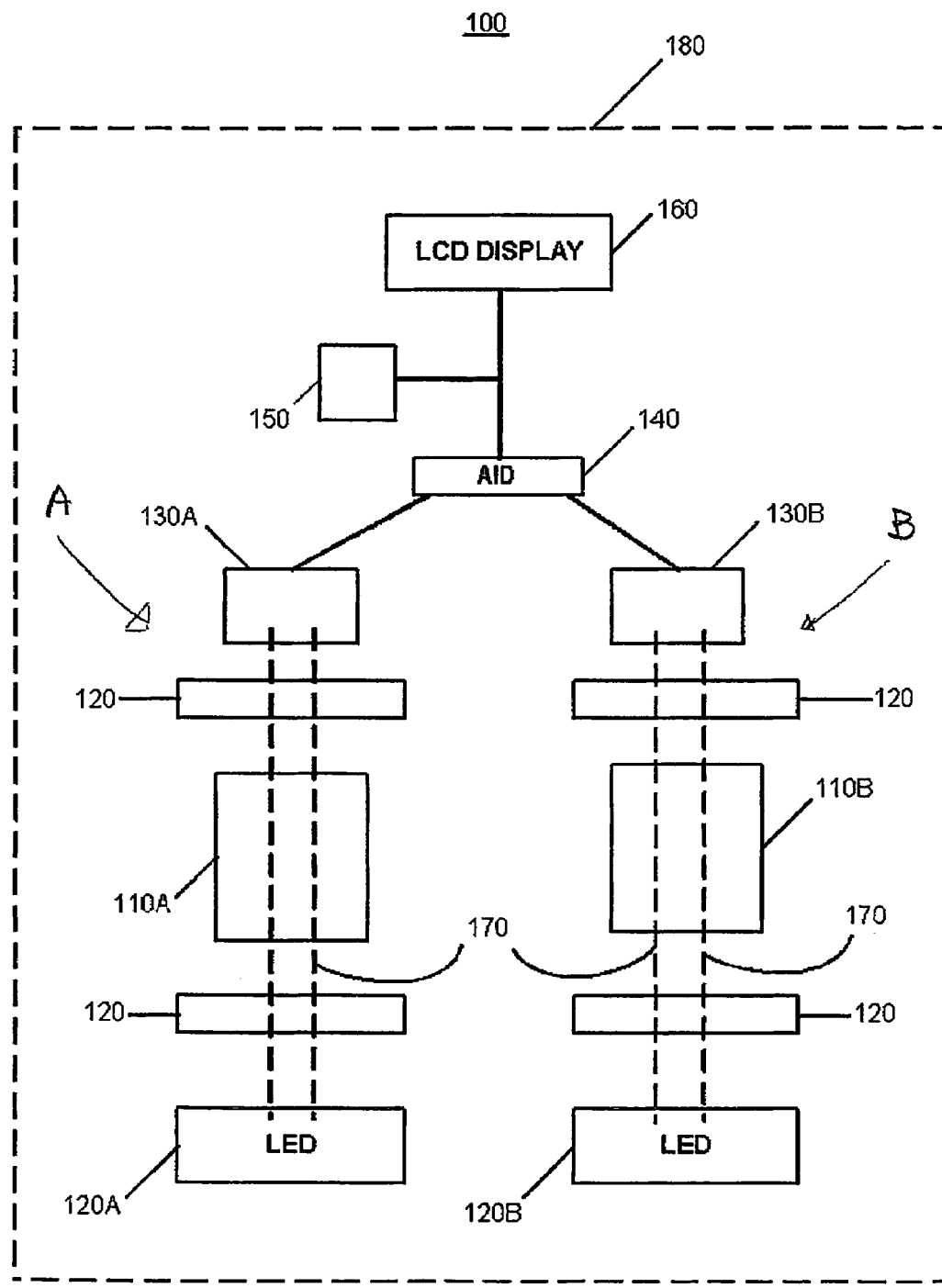
FIG. 1a is a schematic block diagram of a portable two channel colorimetric device for measuring arsenic concentrations in solution in accordance with the principles of the present invention.

The present invention provides devices and methods for the detection of arsenic contamination in groundwater. The devices may be incorporated in kits that are suitable for use in the field, for example, as hand-held colorimeters.

Test and reference solutions are prepared from a water sample using arsenic-selective chemistries. An exemplary colorimeter measures the differential infrared-light absorption between a test solution and a reference solution to obtain a quantitative measurement of the arsenic concentration in the water sample. The chemical preparation methods used to prepare the test and reference solutions are based on an extension of the so-called "Johnson and Pilson method," which is an analytical chemistry technique that was earlier developed for detecting arsenates in the presence of phosphates in seawater. See e.g. Johnson, D. L. "Simultaneous determination of arsenate and phosphate in natural waters," Environmental Science and Technology, 5, pp. 411-14 (1971); and Johnson, D. L., and M. E. Q. Pilson, "Spectrophotometric determination of arsenite, arsenate, and phosphate in natural waters," Analytica Chimica Acta, 58, 289-299 (1972).

The Johnson and Pilson method was designed to correct for the interference of arsenic in a common and widely used procedure for analyzing phosphate concentration (commonly referred to as the "molybdenum-blue method") in natural waters such as seawater. In the molybdenum-blue phosphate assay method, acidic reagents (e.g., an acidified molybdate reagent and potassium antimonyl tartrate) are reacted with soluble phosphates to produce a heteropoly acid (phosphomolybdic acid). The latter is reduced to an intensely blue molybdate color complex by ascorbic acid. The molybdate color complex absorbs light, and its absorption spectrum can be measured spectrophotometrically. Because of the similarity in electronic structure of arsenate (As V) to phosphate (P V), any arsenate (As V) present in solution also enters the molybdate complex and interferes with the measurement of phosphate concentrations.

In the Johnson and Pilson method, to avoid arsenic interference or to correct for its presence, a reduction reaction step (e.g., a thiosulfate reduction) of dissolved arsenate is included in the molybdenum-blue phosphate analysis. The reduction reaction converts all arsenic to its lower oxidation state, arsenite (As III). Arsenite does not react to form the molybdate complex. Thus, true phosphate concentrations can be determined while avoiding interfering arsenate concentrations. Conversely, total arsenic concentrations may be determined by subtracting the absorbance of the molybdate blue complex between an oxidized sample (i.e. with all arsenic compounds converted to arsenates) from that of a reduced sample in which only the phosphates react to form the molybdenum-blue. The determination of the total arsenic concentrations can be difficult because the differential absorbance is usually a very small number.

For determination of arsenic concentrations at the levels of concern in groundwater contamination, application of the conventional Johnson and Pilson method can be particularly difficult because of the higher proportion of phosphates found in groundwater. The phosphate levels in groundwater are generally higher than those found, for example, in seawater, for which the Johnson and Pilson method was originally developed. In Bangladesh, groundwater typically contains an order of magnitude more phosphate (e.g., 5-50 umol/kg) than arsenic (e.g., 5 to 750 µg/L, which corresponds to <0.1-10 umol/kg). Thus, the difference in molybdate blue absorbance between an unreduced water sample and a reduced water sample, can be an order of magnitude or smaller, than the individual absorbances. Conventionally, complex and expensive laboratory spectrophotometers are required to measure the small difference in absorption spectra of the reduced and unreduced samples.

The present method recognizes that the absorption spectra of the molybdate blue complex has a peak or maximum at a wavelength of about 880 nm. Accordingly, an accurate measurement of absorbance at wavelengths of about 880 nm is utilized to determine the molybdate-blue concentrations accurately. Measurements at a fixed wavelength or integrated over a fixed distribution of wavelengths, are carried out using low cost portable colorimeters of simple construction.

FIG. 1A shows a block diagram of an exemplary portable low-cost colorimeter 100 in accordance with the principles of the present invention. Colorimeter 100 may have a two channel configuration (optical probes, or channels A and B) for optical absorbance measurements on two sample aliquots in the same or similar physical environment. The aliquots are placed in optical cuvettes 110A and 110B. Cuvettes 110A and 110B may have a square cross-section, for example, of about 12.7 mm on each square side. Dual infrared radiation sources 120A and 120B generate infrared radiation that is configured to pass through cuvettes 110A and 110B, respectively. Infrared radiation sources 120A and 120B may, for example, be solid-state light emitting diodes. Exemplary sources 120A and 120B may generate radiation beams 170 at wavelengths of about 880 nm. Suitable optics 120 may optionally be used to focus or collimate the radiation entering or leaving cuvettes 110A and 110B. Optics 120 may, for example, be integrated or built into the solid-state light emitting diodes as a lens. Optics 120 may optionally include wavelength filters, beam diffusers, splitters, or any other optical elements used in conventional optics. The radiation that passes through cuvettes 110A and 110B is measured by photodetectors 130A and 130B, respectively. Photodetectors 130A and 130B, may, for example, be solid-state devices that are sensitive to the radiation wavelengths of sources 102A and 120B. The voltage outputs of photodiodes 130A and 130B may be read by a serial analog-to-digital converter 140, for example, for display on an LCD display screen 160. Analog-to-digital converter 140 may, for example, be a 12-bit serial converter with a millivolt resolution. A microcontroller 150 maybe used to control the operation of electronic components such as photodiodes 130A and 130B, to process data, and to control the flow of processed data, to LCD display screen 160 or to other output devices. Microcontroller 150 may, for example, be a programmable interrupt controller (PIC). Microcontroller 150 may be used to read photodetectors 130A and 130B voltages sequentially. Microcomputer 150 may be programmed to calculate the absorbance in each channel or cuvette 110A and 110B relative to pure water standards or blanks.

Figure 1B:
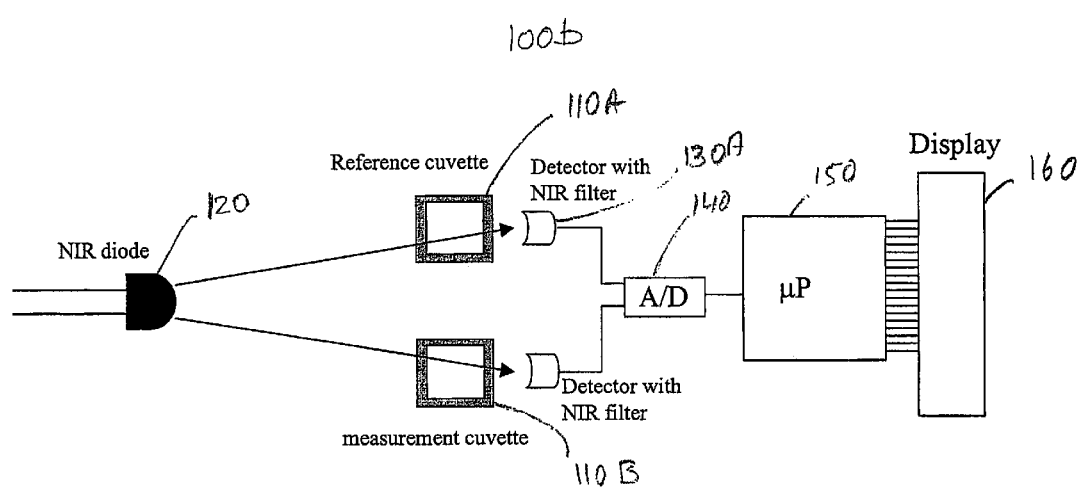
FIG. 1b is a schematic block diagram of a version of the portable two channel colorimetric device utilizing a single light source to form dual light beams in accordance with the principles of the present invention.
Figure 1C:
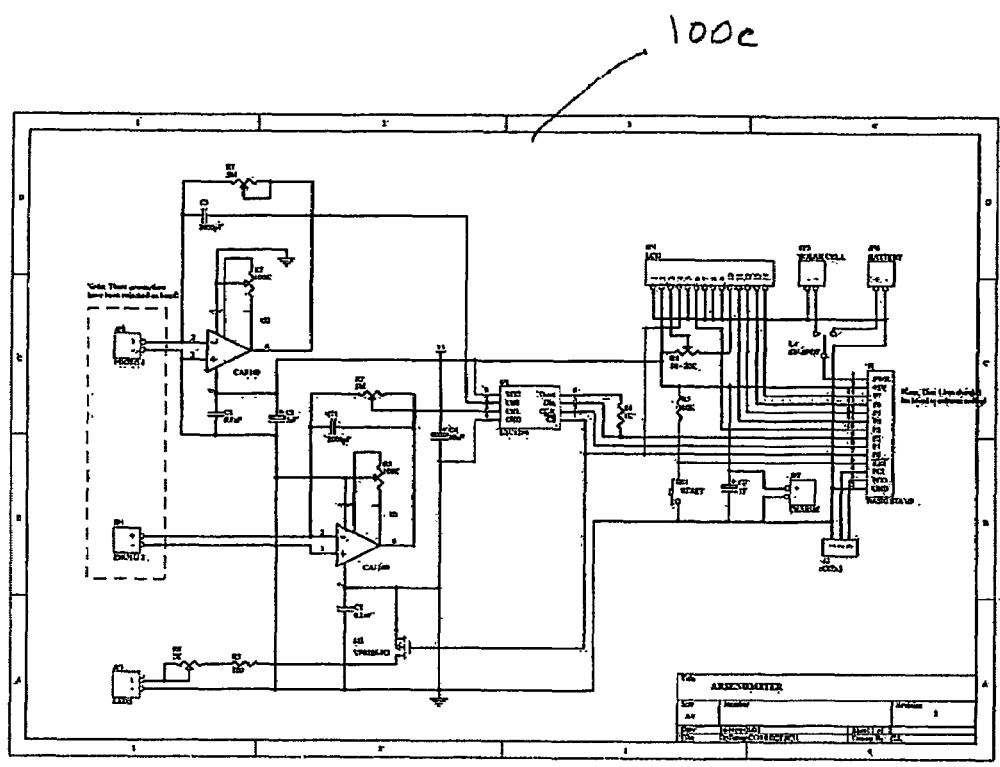
FIG. 1c is an exemplary circuit diagram of the electronic components of a portable colorimetric device in accordance with the principles of the present invention.

It will be readily understood that a particular configuration of electronic and optical-components is shown only for purposes of illustration. Other suitable configurations of electronic and optical components may be used in accordance with the principles of the invention. For example, a single source of radiation may be used to generate radiation, which is split into two beams using passive beam splitting arrangements. FIG. 1b shows, for example, colorimeter 100b having a single near infrared light emitting diode for producing the dual radiation beams. Using a single source of radiation for two measurement channels can be advantageous in differential measurements, for example, by eliminating a possible source of systematic instrument variation or noise between the optical probes in the two channels. All of the electronic and opto-electronic components used in fabricating colorimeter 100 or 100b, may be low power, low cost components that are readily available commercially. FIG. 1c shows a circuit diagram of an exemplary calorimeter circuit fabricated using off-the-shelf electronic components.

An exemplary dual-LED calorimeter 100 (hereinafter referred to as the "the LDEO" unit, in recognition of the Lamont-Doherty Earth Observatory), which was fabricated using commercially available components, operates on a 9V alkaline battery, and has low power requirements (less than 10 ma). The components of the LDEO including the battery (not shown in FIG. 1a) are enclosed in a case 180, which is about the size of a hardcover book. The case may have provisions (e.g., casing holes) for passing dry or desiccating gases over the enclosed electronic components and/or the surfaces of optical elements to avoid any deleterious effects of humidity in field conditions. The entire unit weighs about 500 grams. Cuvettes 110A and 110B extend out from the top cover of the case to allow sample aliquots to be introduced in to them externally, for example, using pipettes.

In operation, to measure the arsenic concentration in a water sample, aliquots of water are treated with chemical acid reagents to develop color (e.g. molybdenum-blue). The aliquots may be prepared externally or in situ, for example, by adding suitable chemical reagents to water samples placed in cuvettes 110A and 110B. An unreduced (or oxidized) aliquot may be placed in one channel (e.g. channel A). A reduced aliquot may be placed in the other channel (e.g. channel B). The absorbance of each channel may be measured from optical measurements in the manner described above. The differential absorbance of reduced and unreduced aliquots, is proportional to the arsenic concentration in the water sample.

Figure 1D:
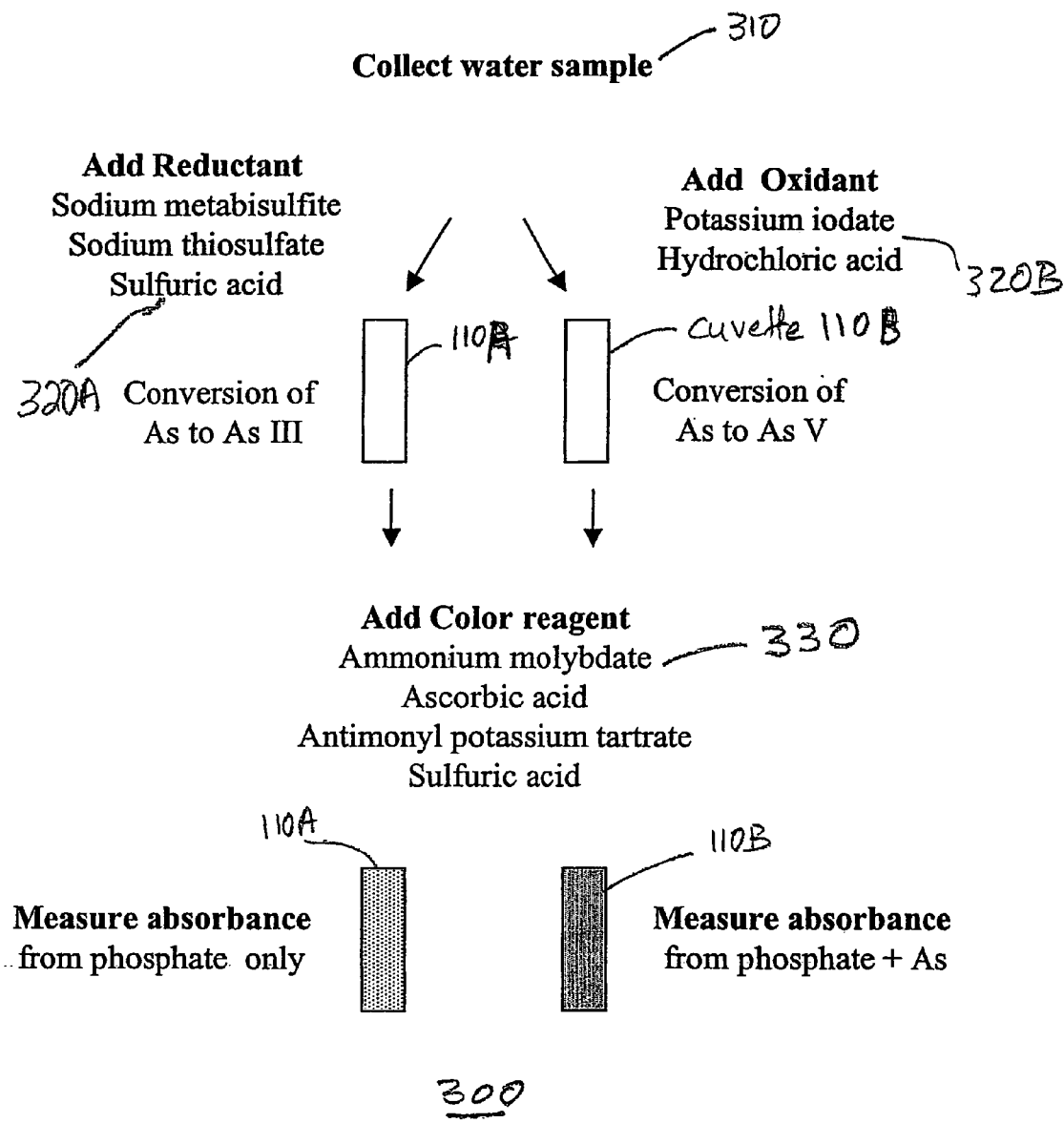
FIG. 1d is an illustrative block diagram showing steps of an analytical method for quantitative determination of arsenic levels in accordance with the principles of the present invention.

FIG. 1d shows, for example, a flow diagram of a procedure 300 that may be used for measuring arsenic concentrations in a water sample using the portable dual channel colorimeters. At step 310 the water sample is collected. At the next step, two sample aliquots are prepared, for example, by using pipettes to transfer measured amounts of the water sample into cuvettes 110A and 110B (not shown). At step 330A, a reducing reagent is dispensed in cuvette 110A to reduce arsenic to its arsenite state. The reducing reagents may, for example, include sodium metabisulfite, sodium thiosulfate and sulfuric acid. At optional step 320B, an oxidizing reagent is dispensed in cuvette 110B, to convert arsenic to its higher oxidation state, arsenate. The oxidizing reagent may, for example, include potassium iodate and hydrochloric acid. After the oxidation and reduction steps, at step 330, color reagents are added to the two cuvettes. The color reagent may, for example, include ammonium molybdate, ascorbic acid, antimonyl potassium tartrate and sulfuric acid. The proportion of antimonyl potassium tartrate in the color reagents, may be increased over conventional Johnson and Pilson formulations in consideration of the high phosphate content of groundwater samples. At steps 340A and 340B, measurements of the absorbance of the sample aliquots in cuvettes 110A and 110B may be conducted, for example, by recording or observing the photodetector output voltages. A photodetector output voltage may be converted to an absorbance value using normalized voltage values, according to the known equation:

$$\text{Absorbance} = -\ln(I_{sample}/I_{blank}) = -\ln(V_{sample}/V_{blank})$$

where $I_{sample}$ and $I_{blank}$ are the intensity of light passing through the sample and a blank reference solution respectively, and $V_{sample}$ and $V_{blank}$ are the corresponding voltage readings from the detector. Further, according to Beer's Law, the absorbance by a light-absorbing complex in solution, is proportional to its concentration. Thus, the photodetector voltage readings may be converted to molybdenum-blue concentration values, using suitable proportionality factors which can be obtained by suitable calibration of the colorimeter.

Exemplary procedures that may be used for calibration of a colorimeter are described herein with reference to operation of the LDEO unit as a concrete example. It will be understood that LDEO unit is used as an example for purposes of illustration only. The principles of the calibration procedures are universally applicable.

Calibration And Testing Of The LDEO Unit

A. The Intrinsic Detection Capabilities Of The LDEO Unit.

The intrinsic detection capabilities of the LDEO unit were tested in laboratory conditions. The LDEO unit included a 12-bit analog-to-digital converter (140) capable of 1 millivolt resolution. Test aliquots, used to test the instrument capabilities included pure water solutions and solutions produced by reacting Bangladesh groundwater samples containing phosphate and arsenic. The range of groundwater samples tested covered the dynamic range of naturally occurring phosphate levels (i.e. 5-50 uM) found in Bangladesh.

The optical and electronic capabilities of the unit were assessed in the laboratory, by comparing detector output voltage readings for a series of identical solutions placed simultaneously in both cells. First, the reproducibility of absorbance measurements was tested by repeated measurements on pure water solutions. Reproducible photodetector voltage readings of 1300±1 mV (σ=±0.07%) were obtained for pure water. Similar repeated measurements on highest-phosphate content groundwater samples yielded voltage readings 200±1 mV (σ=±0.5%). The higher standard deviation in groundwater voltage readings (i.e. σ=±0.5%) can be attributed to the limited measurement precision corresponding to the number of significant digits displayed on LCD display 160 (±1 mV).

Next, pairs of identical test solutions of a series of groundwater samples having various concentrations of phosphates that were pre-treated to form molybdenum-blue phosphate complexes, were placed in cuvettes 110A and 110B. For each solution in the pair, transmitted light photodetector voltage readings were normalized and converted into absorbance values using the formula:

$$\text{absorbance} = -\ln(\text{voltage reading for test solution}/\text{voltage reading for pure water}).$$

Figures 2A, 2B:
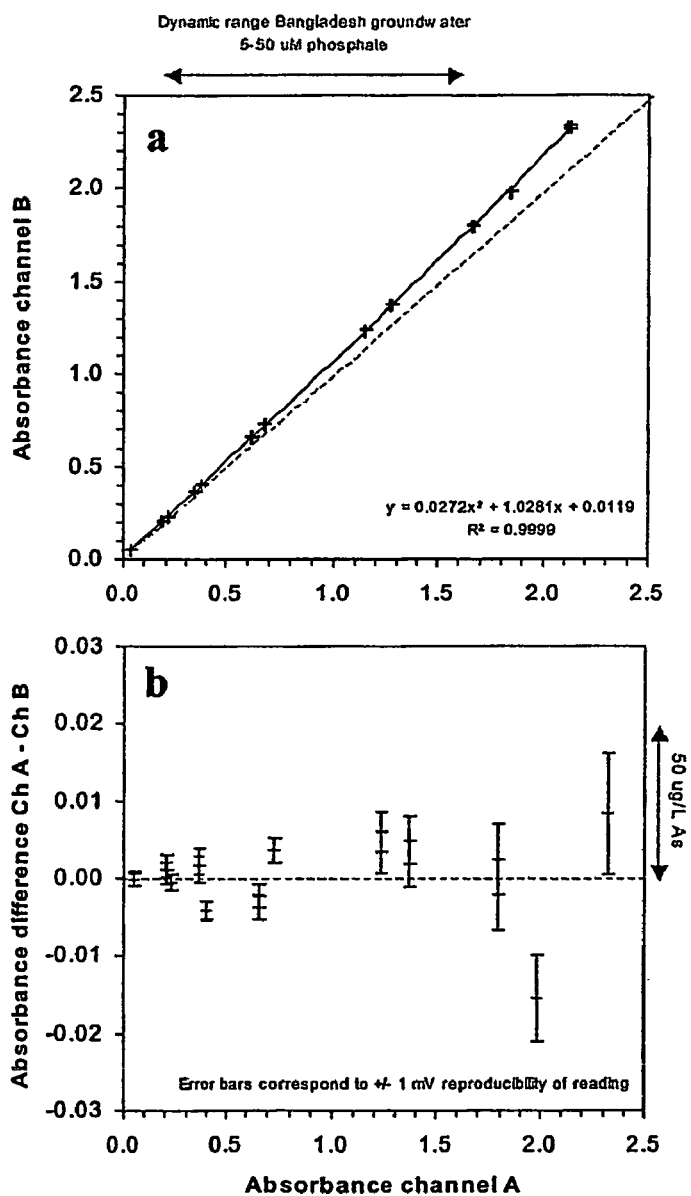

FIG. 2a shows a graph of absorbance values measured in channel B, plotted as a function of the values measured in channel A.

Repeated absorbance measurements of the same solution in the same channel rarely differed by more than 1 mV (corresponding to the last significant figure of LCD display 160). This result was obtained for both cases, one where a solution was introduced in a cuvette and repeatedly measured, and two where a cuvette was refilled with a solution from the same pre-treated groundwater sample as the preceding solution measured. This variation in the photodetector readings of ±1 mV are reflected as the small error bars in the absorbance values shown in FIGS. 2a and 2b.

However, comparison of the measured absorption values for pairs of identical solutions measured in the two channels, showed a systematic offset in the response of the two channels. A one-to-one correlation (represented by the dashed line in FIG. 2a) may be expected under ideal conditions if both channels were identical. As seen from FIG. 2a, response of the two channels A and B, deviates from a one-to-one relationship. The non-identical or unequal responses of the two channels can be attributed to physical differences in the two channels, (e.g., in optical path lengths) or to other differences (e.g., variations in radiation beam quality or shape).

To compensate for the effects of the unequal responses of the two channels on differential measurements, the responses of the two channels may be normalized with respect to each other. For this purpose, the measurement response of one channel (e.g., channel B) was fitted to the measurement response of the other channel (e.g., channel A). A quadratic function, $y=0.0272x^2+1.0281x+0.0119$, was found to give a satisfactory fit (e.g., solid line FIG. 2a). This fitting function was used to normalize the measurement data from channel B, relative to measurement data from channel A.

FIG. 2b, shows a graph of the residual absorbance difference, using the normalized measurement data for the pairs of identical solutions measured in channels A and B. The residual absorbance difference data shows scatter about an ideal zero-difference line that may be expected of identical solutions measured in the two identical (or normalized) channels A and B. The standard deviation of the data in FIG. 2b has a value within +/−0.001.

The scatter in the data about an ideal zero-difference line may be attributed to the least count or minimum resolution of ±1 mV of the photodetector voltage readings. To confirm this, an expected error in the residual absorbance difference between the two channels, was computed assuming a ±1 mV least count or precision uncertainty in the voltage readings for one of the channels. Because of the logarithmic relation between voltage readings and absorbance, the effect of this uncertainty is amplified from about ±0.001 at low absorbance (i.e. low phosphate content samples), to about ±0.010 at high absorbance (e.g., high phosphate content samples with absorbance above 2.0). Comparison of the computed uncertainty with the scatter of absorbance difference data about the ideal zero-difference line (FIG. 2B) suggests that the scatter is primarily due to the ±1 mV resolution of LCD display 160.

Encouragingly, the magnitude of the scatter, when compared to absorbance difference corresponding to a 50 µg/L arsenic water sample, suggested that a 10 µg/L detection limit could be attained with the LDEO unit, particularly when the absorbance value was in the 0-1.5 range. To confirm this, a spiked test solution containing 50 µg/L arsenic was tested. A typical absorbance difference value of 0.020 was obtained between the two channels. Using this measured absorbance difference value, and assuming that the error in absorbance difference measurements may be as large as three times the computed error due to the 1 mV resolution of LCD display 160, the arsenic detection limits of the LDEO unit can be estimated. The arsenic detection limits are estimated to be about 8-80 µg/L arsenic, across the natural range phosphate concentrations found in Bangladesh.

B. Effects Of Humidity And Dry Nitrogen Gas Purges.

Figure 3A:
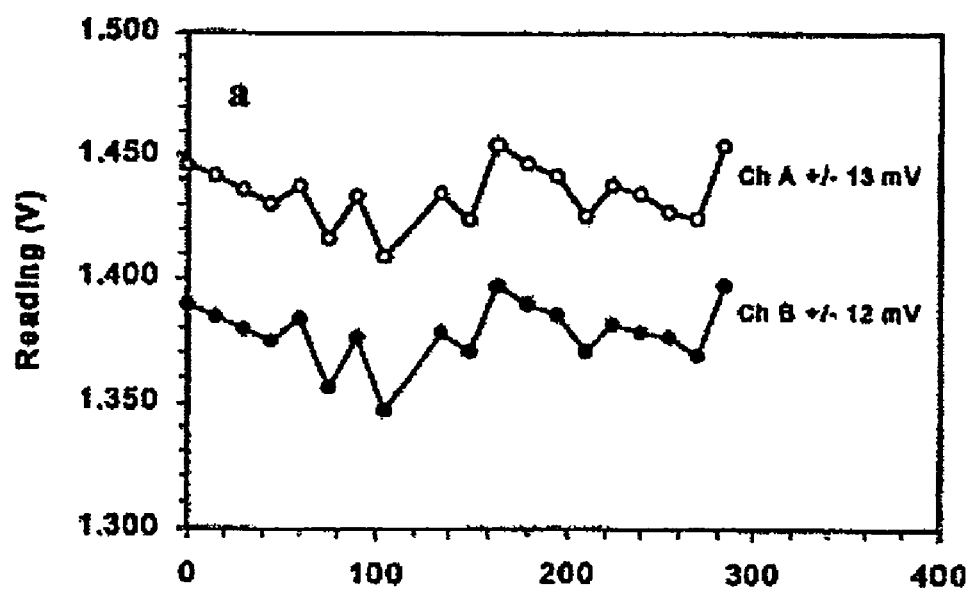
Figure 3B:
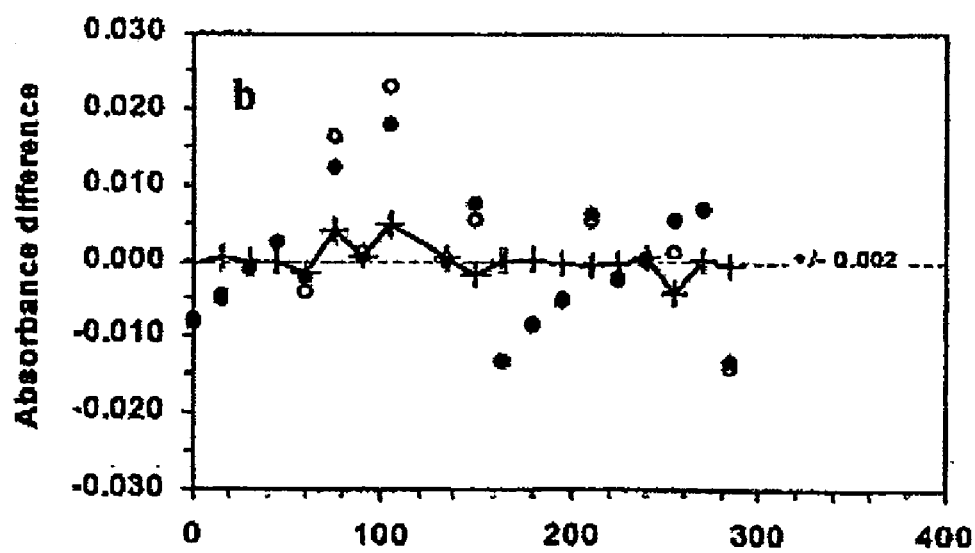

The LDEO unit was field tested in Bangladesh during the local monsoon season. The unit was unpacked in extremely humid air. Repeat measurements on test aliquots, showed that the standard error of repeated individual readings from either channel A and B, increased by an order of magnitude over previous tests under laboratory conditions in the U.S. (FIG. 3a). The standard error for absorbance differences for water solutions between the two channels (FIG. 3b), however, increased only by a factor of two, relative to earlier laboratory tests, (i.e. +/−0.001, FIG. 2B). This observation suggested that both LEDs 120A and 120B were commonly affected. Dry nitrogen gas was fed through a hole in case cover 180 of the LDEO unit. The initial reproducibility (laboratory conditions) for both individual channels, was regained after the LDEO unit was purged with dry nitrogen for several hours. This suggested that elevated humidity affected the common power supply causing a similar degradation of the performance of both LEDs 120A and 120B. Thus, robust performance of the colorimeter may be expected with use of power supply circuits that are not affected by humidity. Additionally or alternatively, to minimize the effects of humidity, casing 180 may be sealed enclosing a moisture-absorbing agent or desiccant (e.g., silica gel).

C. Kinetics Of Color Development And Reagent Stability.

Chemical reagents were added to groundwater aliquots in cuvettes 110A and 110B to convert phosphates and arsenates into molybdate blue complexes. Using chemical reagents (e.g., the molybdate reagent) in the conventional proportions (e.g., as prescribed by Johnson and Pilson), up to two hours were required for full or complete development of color. As previously mentioned, the Johnson and Pilson method chemical recipes were originally formulated for testing seawater, in which phosphate concentrations typically are only about one-tenth of the values found in groundwater.

In the procedures for testing groundwater using the LDEO unit, the proportion of potassium antimonyl tartrate in the color reagent, was increased by about a factor of ten over the conventional Johnson and Pilson reagent formulations. With this increased proportion, the time required for full color development in both reduced and oxidized water aliquots, decreased to about 5 minutes for freshly made reagents and to about 15 minutes for "day-old" reagents.

Figures 4A, 4B:
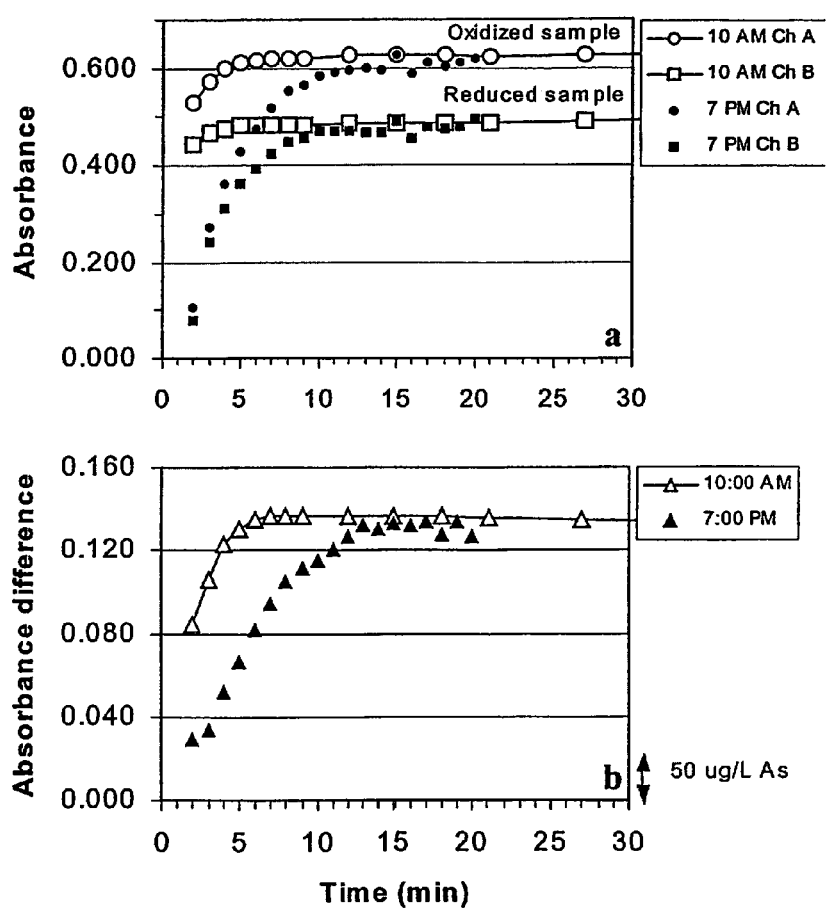

In an experimental run, the time course for color development was followed after adding freshly prepared color reagents to a pair of test samples in the LDEO unit (see e.g., step 330, FIG. 1D). The test samples were oxidized and reduced aliquots of a Bangladesh groundwater sample containing about 350 µg/L arsenic. The color development was determined by measuring absorbance. The same experiment was repeated, after the color reagents had been exposed to field conditions for about nine hours in the course of the day. FIGS. 4a and 4b show measured absorbance and differential absorbance values as a function of time. The measured values plateau, after about five, to about fifteen minutes, depending on the age of the reagents. The freshness of the reagents affects the reaction times necessary to reach steady state values. Keeping the reagents in an cool and dark environment in the field may reduce this effect, and yield reaction times that are less sensitive to the age of the reagents. The steady-state absorbance values themselves, may be independent of the reagent age, or freshness as indicated by the flat plateaus in FIGS. 4a and 4b. In any case, FIGS. 4a and 4b suggest that, a five to fifteen minute reaction time may be sufficient for full color development and correspondingly for the measurement of steady state absorbance values in most instances of groundwater testing.

D. Effects Of Sample Pre-Treatment By Oxidation Or Reduction.

Figures 5A, 5B:
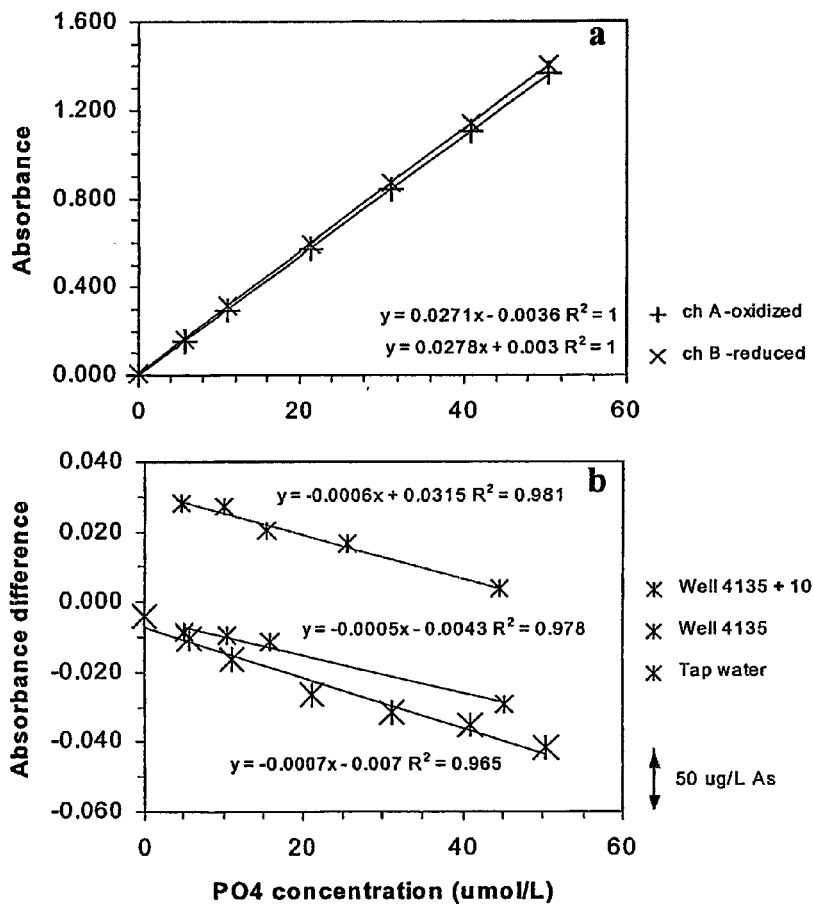

Further evaluation of the LDEO unit revealed an effect of sample pre-treatment. A basic assumption of the Johnson and Pilson method is that sample pre-treatment by either oxidation or reduction, does not significantly affect subsequent color development for either phosphate color complexes (i.e. reduced samples), or phosphate+arsenate color complexes (i.e., oxidized samples). Incremental additions of phosphate to laboratory tapwater containing no detectable arsenic, showed this was not the case. An apparent decline in absorbance with increasing phosphate concentrations was measured with the LDEO unit. The reduced sample systematically yielded 2.5% higher absorbances than the oxidized sample (FIGS. 5a and 5b)). The effect of increasing phosphate concentrations, were confirmed by repeating the experiment with a Bangladesh groundwater sample containing undetectable levels of arsenic (well 4135) and also with the same sample spiked with 50 µg/L of arsenic (FIG. 5b).

In the present chemical analysis using the dual beam colorimeter, the effect of sample pre-treatment may be compensated for, by multiplying the absorbances measured or oxidized samples by 1.025. Alternatively, the effect may be eliminated completely by a suitable choice of the proportion of reagents used to pre-treat the samples.

E. Calibration Of Measured Arsenic Levels Against Standard Laboratory Measurement Techniques.

Figure 6:
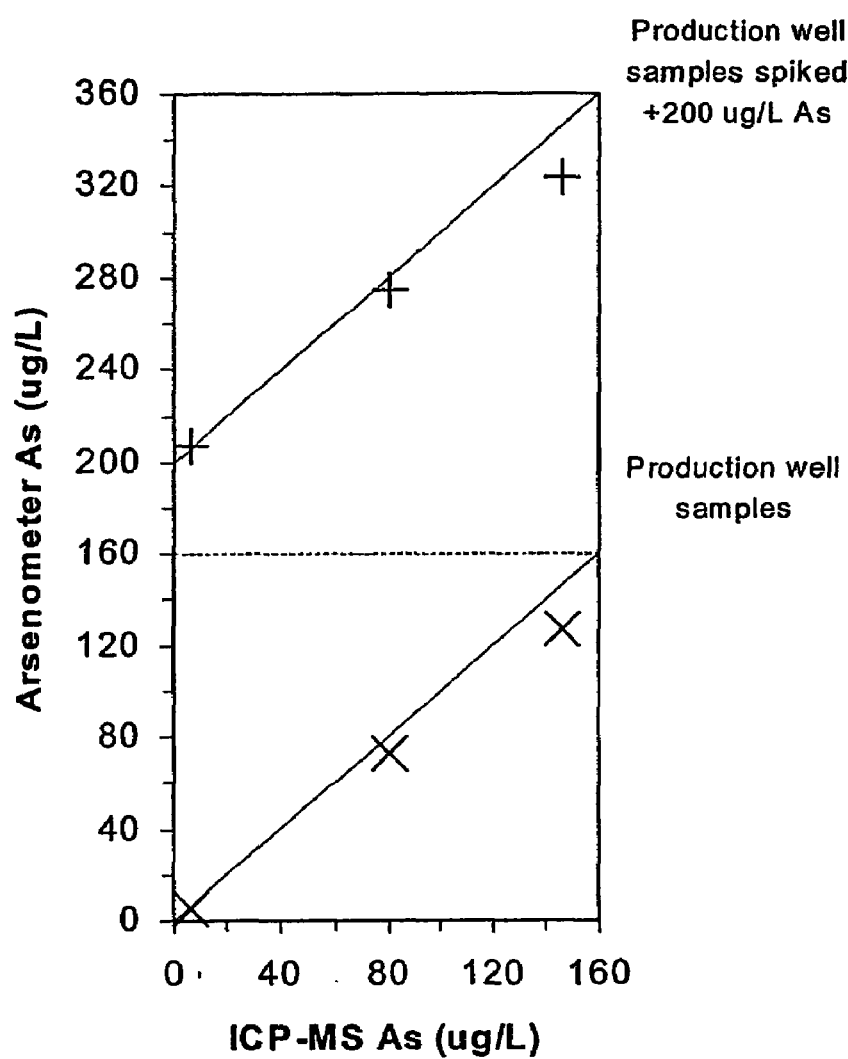
FIG. 6 is a graph illustrating the co-relation between arsenic levels measured by the portable colorimeter of FIG. 1a and arsenic levels that are measured in the same samples measured by two different laboratory methods.

Arsenic levels measured in the field, were calibrated against measurements made in laboratory conditions, using standard analytical techniques for determining absolute arsenic concentrations. Three production well water samples collected in Bangladesh were analyzed in the field. The arsenic levels in aliquots of the three samples were determined using the LDEO unit. The measured arsenic levels ranged from about 5 to about 120 µg/L. This range of arsenic levels, is below the reliable detection limits of standard laboratory analytical techniques for determining absolute arsenic concentrations (e.g., graphite-furnace atomic absorption (AAS) and high-resolution inductively coupled plasma-mass spectrometry (ICP-MS). Therefore, other aliquots of each of the three well water samples, were spiked with standard additions to increase the arsenic concentration in each sample by about 200 µg/L to bring them within range of the reliable detection limits. The spiked aliquots were later analyzed by the standard AAS and ICP-MS techniques in a U.S. laboratory. A good co-relation between the field measurements and the laboratory measurements was obtained. FIG. 6 shows the co-relation between the arsenic levels measured in the field and in the laboratory. The absolute arsenic concentrations obtained from the field measurements using the LDEO unit, differ by no more than 20 µg/L from the laboratory measurements. The internal precision of the field method, may be estimated from the relative standard deviation of absorbance differences, caused by additions of 200 µg/L arsenic to each of the three samples. This internal precision is estimated to be about±1.5% (±3 µg/L As).

It will be understood, that the foregoing is only illustrative of the principles of the invention, and that various modifications can be made by those skilled in the art, without departing from the scope and spirit of the invention, which is limited only by the claims that follow.

The invention claimed is:

1. A method for quantitative determination of arsenic concentration in a water sample in the field, wherein the water sample comprises phosphates that have an order of magnitude or more higher concentration than the arsenic concentration, the method comprising:
    (a) preparing a first and a second water sample aliquot;
    (b) adding a reducing agent to the first water sample aliquot to reduce arsenic in the aliquot to an arsenite state, whereas the second water sample aliquot is unreduced;
    (c) adding a color reagent to the first and second sample aliquots, whereby phosphates in the first aliquot and both phosphates and arsenates in the second aliquot are converted into color complexes;
    (d) using optical probes to measure light absorbance of the color complexes formed in each aliquot; and
    (e) using the measured light absorbances for the two aliquots to determine the arsenic concentration in the groundwater sample,
    wherein the optical probes are disposed in a portable battery-powered colorimeter, and wherein the determination of the arsenic concentration has a detection limit of 10 ug/L or lower for groundwater samples having phosphate concentrations in the range of 5-50 µM.

2. The method of claim 1, further comprising the step of adding an oxidizing agent to the second sample aliquot to oxidize arsenic in the aliquot to an arsenate state.

3. The method of claim 1 wherein the optical probe comprises infrared radiation having a wavelength of about 880 nm.

4. The method of claim 1 wherein the color complexes comprise molybdenum blue.

5. The method of claim 4 wherein the color reagent comprises potassium antimonyl tartrate, wherein the water sample is a groundwater sample, and wherein the proportion of color reagents added to groundwater sample aliquots is increased by about a factor of 10 over conventional Johnson and Pilson formulations used for seawater analysis.

6. The method of claim 1 wherein an optical probe comprises:
    a cuvette to hold a sample aliquot;
    a light emitting diode which is configured to radiate light on to the cuvette;
    a photodetector for measuring the intensity of light transmitted through the held sample aliquot; and
    an electronic component to process the voltage output of the photo detector.

7. The method of claim 1 wherein using optical probes comprises using a pair of optical probes that are disposed in a dual-beam arrangement in the portable colorimeter, and using a first probe in the pair to measure light absorbance in the first sample aliquot, and the second probe in the pair to measure light absorbance in the second sample aliquot.

8. The method of claim 7 wherein the responses of the optical probes in the pair are normalized with respect to each other.

9. The method of claim 1 wherein the light absorbance in the first and the second sample aliquots is measured sequentially.

10. The method of claim 1 wherein the light absorbance in the first and second sample aliquots is measured concurrently.

* * * * *

UNITED STATES PATENT AND TRADEMARK OFFICE
CERTIFICATE OF CORRECTION

| | | |
|---|---|---|
| PATENT NO. | : 7,336,362 B2 | |
| APPLICATION NO. | : 10/523568 | |
| DATED | : February 26, 2008 | |
| INVENTOR(S) | : Van Geen | |

It is certified that error appears in the above-identified patent and that said Letters Patent is hereby corrected as shown below:

IN THE SPECIFICATION:
On Page 1, Column 1, line 13, please insert the following header and paragraph:

-- Statement Regarding Federally Sponsored Research or Development
This invention was made with government support under grant number ES010349 awarded by the National Institutes of Health. The government has certain rights in the invention. --

Signed and Sealed this

Twenty-fourth Day of June, 2008

JON W. DUDAS
*Director of the United States Patent and Trademark Office*